US007112437B2

(12) United States Patent
Pera

(10) Patent No.: US 7,112,437 B2
(45) Date of Patent: Sep. 26, 2006

(54) METHODS OF CULTURING EMBRYONIC STEM CELLS AND CONTROLLED DIFFERENTIATION

(75) Inventor: Martin Frederick Pera, Prahran (AU)

(73) Assignee: ES Cell International Pte Ltd., Singapore (SG)

( * ) Notice: Subject to any disclaimer, the term of this patent is extended or adjusted under 35 U.S.C. 154(b) by 46 days.

(21) Appl. No.: 09/885,679

(22) Filed: Jun. 20, 2001

(65) Prior Publication Data

US 2002/0022267 A1     Feb. 21, 2002

(30) Foreign Application Priority Data

Jun. 20, 2000   (AU) ..................... PQ8242
Nov. 8, 2000    (AU) ..................... PR1327

(51) Int. Cl.
    *C12N 5/02*   (2006.01)
(52) U.S. Cl. .................. 435/325; 435/1.1; 435/405
(58) Field of Classification Search ........... 435/325, 435/1.1, 405; 800/3, 4
    See application file for complete search history.

(56) References Cited

U.S. PATENT DOCUMENTS

| 5,843,775 | A  | * | 12/1998 | Valenzuela et al. ......... 435/325 |
| 5,843,780 | A  | * | 12/1998 | Thomosn ..................... 435/363 |
| 6,087,168 | A  |   | 7/2000  | Levesque et al. |
| 6,245,564 | B1 | * | 6/2001  | Goldman et al. ........... 435/368 |
| 6,686,198 | B1 | * | 2/2004  | Melton et al. .............. 435/377 |
| 6,949,380 | B1 | * | 9/2005  | Levesque et al. ........... 435/325 |
| 2002/0019046 | A1 | * | 2/2002 | Carpenter et al. ........... 435/368 |

FOREIGN PATENT DOCUMENTS

CA    2174098    4/1995

WO    WO 98/30679    7/1998

OTHER PUBLICATIONS

Shou e tal. Development 127:5403-5413 (2000).*
Gratsch et al. Developmental Biology 245:83-94 (2002).*
Mehler et al. Developmental Neuroscience 22:74-85 (2000).*
Watson et al. Cell Structure and Function 26:123-129, (2001).*
Shen The Journal of Clinical Investigations 112(4):500-502, (Aug. 2003).*
Lim, D. et al., "Noggin Antagonizes BMP Signaling to Create a Niche for Adult Neurogenesis", *Neuron* 28: 713-726 (2000).
Finley, M. et al., "BMP-4 Inhibits Neural Differentiation of Murine Embryonic Stem Cells", *J. Neurobiol.* 40: 271-287 (1999).
Ashton, Dr. Brian, "Noggin, A BMP Antagonist, Increases Proliferation, Differentiation And Mineralisation In Human Marrow Mesenchymal Stem Cells", *International Conference Bone Morphogenetiv Proteins 2000*, Jun. 7-11, 2000 (Abstract).
Harland, Richard, "Noggin: Molecular Developmental Biology" *International Conference Bone Morphogenetic Proteins 2000*, Jun. 7-11, 2000 (Abstract).
Pera, Martin F., et al., "Human embryonic stem cells", *Journal of Cell Science*, 113: 5-10, (2000).

* cited by examiner

*Primary Examiner*—Joseph Woitach
(74) *Attorney, Agent, or Firm*—Scully, Scott, Murphy & Presser, P.C.

(57) ABSTRACT

The present invention provides a preparation of undifferentiated embryonic stem (ES) cells sustainable for a prolonged period in an undifferentiated state which will undergo stem cell renewal or somatic differentiation. Preferably the cells are capable of somatic differentiation in vitro and are inclined to differentiate away from an extraembryonic lineage. The present invention also provides method of culturing embryonic stem (ES) cells to improve stem cell maintenance and persistence in culture. The method also provides a culture of ES cells prepared by the method as well as differentiated cells derived from the embryonic cells resulting from directed differentiation procedures provided by the present invention.

19 Claims, 17 Drawing Sheets

Gene Expression in ES and ES/Noggin cells (2)

METHODS OF CULTURING EMBRYONIC STEM CELLS AND CONTROLLED DIFFERENTIATION

The present invention relates to a method of culturing embryonic stem cells particularly to improve stem cell maintenance and persistence in culture. The method also provides a culture of embryonic stem cells prepared by the method as well as differentiated cells derived from the embryonic cells resulting from directed differentiation procedures provided by the present invention.

INTRODUCTION

The production of human embryonic stem cells which can be either maintained in an undifferentiated state or directed to undergo differentiation into extraembryonic or somatic lineages in vitro allows for the study of the cellular and molecular biology of early human development, functional genomics, generation of differentiated cells from the stem cells for use in transplantation or drug screening and drug discovery in vitro.

In general, stem cells are undifferentiated cells which can give rise to a succession of mature functional cells. For example, a haematopoietic stem cell may give rise to any of the different types of terminally differentiated blood cells. Embryonic stem (ES) cells are derived from the embryo and are pluripotent, thus possessing the capability of developing into any cell.

Much attention recently has been devoted to the potential applications of stem cells in biology and medicine. The properties of pluripotentiality and immortality are unique to ES cells and enable investigators to approach many issues in human biology and medicine for the first time. ES cells potentially can address the shortage of donor tissue for use in transplantation procedures, particularly where no alternative culture system can support growth of the required committed stem cell. However, it must be noted that almost all of the wide ranging potential applications of ES cell technology in human medicine-basic embryological research, functional genomics, growth factor and drug discovery, toxicology, and cell transplantation are based on the assumption that it will be possible to grow ES cells on a large scale, to introduce genetic modifications into them, and to direct their differentiation. Present systems fall short of these goals. Present systems for the growth of human embryonic stem cells include the use of Dulbecco's modified Eagle's medium as a basal media with the addition of amino acids and beta mercaptoethanol, serum supplementation, and embryonic mesenchymal feeder cell support. Growth under these conditions is not sufficient for many applications including scaleup of cultures and cloning of single cells, the latter being necessary for selection of transformants following genetic manipulation. Moreover, under present growth conditions, stem cells often follow a default pathway of differentiation into an epithelial cell type that grows either as flat squamous cells attached to the surface of the dish, or in cysts. It is likely that this form of differentiation represents extraembryonic endodermal differentiation and it is postulated that this cell type resembles the primary yolk sac cells of the primate embryo. As noted previously, conditions in which this form of differentiation predominates are unfavourable for differentiation of ES cells into desired somatic cell types.

It would be desirable to control the differentiation pathways to maintain the cells in an undifferentiated state and direct the differentiation to the type of cell when required.

Prior to differentiation, genetic manipulation of the ES cells may be conducted. However, it has been difficult to maintain the cells in the undifferentiated stem cell stage and prevent a default pathway to extraembryonic differentiation. Where somatic lineages are desired, a means of regulating against extraembryonic differentiation of ES cells is an important aspect in governing the fate of the cell. More importantly, greater control of the differentiation process is achieved when various stages of the differentiation process are regulated for instance, at a progenitor cell stage.

Accordingly, it is object of the present invention to overcome or alleviate some of the problems of the prior art and to achieve some regulation of the differentiation process of ES cells to somatic or extraembryonic lineages.

SUMMARY OF THE INVENTION

In a first aspect of the present invention there is provided a preparation of undifferentiated embryonic stem cells sustainable for a prolonged period in an undifferentiated state which favour enhanced stem cell renewal and preferably somatic differentiation. Preferably the cells are capable of somatic differentiation in vitro and are inclined to differentiate away from extraembryonic lineage.

Embryonic stem cells have a natural capacity to differentiate into cells similar to those found in extraembryonic endodermal lineages of the early embryo. Accordingly, if the cells are not treated to prevent this default differentiation pathway, somatic lineages cannot be effectively attained or maintained in vitro for further studies or manipulation. It is desired to maintain the cells in an undifferentiated state giving greater capacity for manipulation of differentiation particularly into somatic lineages.

In another aspect of the present invention, there is provided a method of culturing undifferentiated embryonic stem cells, said method including:

obtaining a source of undifferentiated embryonic stem cells; and culturing the embryonic stem cells in the presence of an indirect or direct antagonist of a BMP-mediated default pathway of extraembryonic endoderm differentiation.

In the preferred embodiment, the present invention provides a method of culturing undifferentiated embryonic stem cells, said method including:

obtaining a source of undifferentiated embryonic stem cells; and culturing the embryonic stem cells in the presence of an indirect or direct antagonist of a BMP-2 mediated default pathway of extraembryonic endoderm differentiation.

Accordingly, in a preferred embodiment of the present invention, there is provided a method of culturing undifferentiated embryonic stem cells, said method including:

obtaining a source of undifferentiated embryonic stem cells; and culturing the embryonic stem cells in the presence of noggin.

In another aspect of the present invention, there is provided a method of producing a progenitor cell from an embryonic stem (ES) cell, said method comprising:

obtaining a source of undifferentiated embryonic stem cells; and culturing the embryonic stem cells in the presence of an antagonist of a BMP mediated default pathway of extraembryonic endoderm differentiation for a period sufficient to differentiate the ES cell to a progenitor cell.

In yet another aspect of the present invention there is provided a method of producing a somatic cell from an ES cell, said method comprising:

obtaining a source of undifferentiated embryonic stem cells;

culturing the embryonic stem cells in the presence of an antagonist of a BMP mediated default pathway of extra embryonic endoderm differentiation for a period sufficient to differentiate the ES cell to a progenitor cell;

obtaining a progenitor culture medium derived from another culture of a somatic progenitor;

culturing the progenitor cell in the progenitor culture medium; and obtaining a somatic cell from a lineage of the somatic progenitor.

In yet another preferred embodiment of the present invention there is provided a method of culturing undifferentiated embryonic stem cells, said method including:

obtaining a source of undifferentiated embryonic stem cells; and culturing the embryonic stem cells in the presence of noggin and a cell derived insulin or insulin analogue factor.

In another aspect of the present invention there is provided a method of culturing undifferentiated embryonic stem cells, said method including:

obtaining a source of undifferentiated embryonic stem cells; and culturing the embryonic stem cells in the presence of a cell derived insulin or insulin analogue induced factor.

In another aspect of the present invention there is provided a method of culturing undifferentiated embryonic stem cells, said method including:

obtaining a source of undifferentiated embryonic stem cells; and culturing the embryonic stem cells in the presence of insulin or an insulin analogue.

In yet another aspect of the present invention there is provided a method of culturing undifferentiated embryonic stem cells, said method including:

obtaining a source of undifferentiated embryonic stem cells; and culturing the embryonic stem cells in the presence of a fibroblast and insulin or an insulin analogue.

Accordingly, this aspect of the invention provides a method for culturing embryonic stem cells so as to enhance stem cell survival and growth during routine culture and to enhance the extent and variety of somatic cells obtained under differentiation conditions.

In another aspect of the present invention there is provided a method of culturing undifferentiated embryonic stem cells capable of somatic differentiation in vitro, said method including:

obtaining a source of undifferentiated embryonic stem cells; and culturing the embryonic stem cells in the presence of a cell derived insulin or insulin analogue induced factor.

Preferably the cells deriving the factor are fibroblasts or embryonic stem cells.

In another aspect of the present invention there is provided a method of culturing undifferentiated embryonic stem cells capable of somatic differentiation in vitro, said method including:

obtaining a source of undifferentiated embryonic stem cells; and culturing the embryonic stem cells in the presence of fibroblast cells and insulin or an insulin analogue.

In another aspect of the present invention there is provided a method of culturing undifferentiated embryonic stem cells capable of somatic differentiation in vitro, said method including:

obtaining a source of undifferentiated embryonic stem cells; and culturing the embryonic stem cells in the presence of insulin or an insulin analogue.

In another aspect of the present invention, there is provided a cell derived insulin or insulin analogue induced factor capable of maintaining embryonic stem cells in an undifferentiated state but favouring somatic differentiation. The cells deriving the factor may be fibroblasts or cultures containing embryonic stem cells.

In yet another preferred embodiment of the present invention there is provided a method of culturing undifferentiated embryonic stem cells, said method including:

obtaining a source of undifferentiated embryonic stem cells; and culturing the embryonic stem cells in the presence of an antagonist BMP mediated default pathway of extraembryonic endoderm differentiation and a cell derived insulin or insulin analogue induced factor.

In another aspect there is provided a differentiated committed progenitor cell line capable of differentiation into somatic cells.

In another aspect, there is provided a somatic cell capable of differentiation in vitro from an undifferentiated embryonic stem cell. There is also provided a committed somatic cell capable of giving rise to mature somatic cells. The cells may differentiate into embryonic mesoderm and embryonic endoderm lineages, including, but not limited to cartilage, muscle, bone, hepatocyte, pancreatic islet cells and respiratory endothelium.

FIGURES

Figure 4:
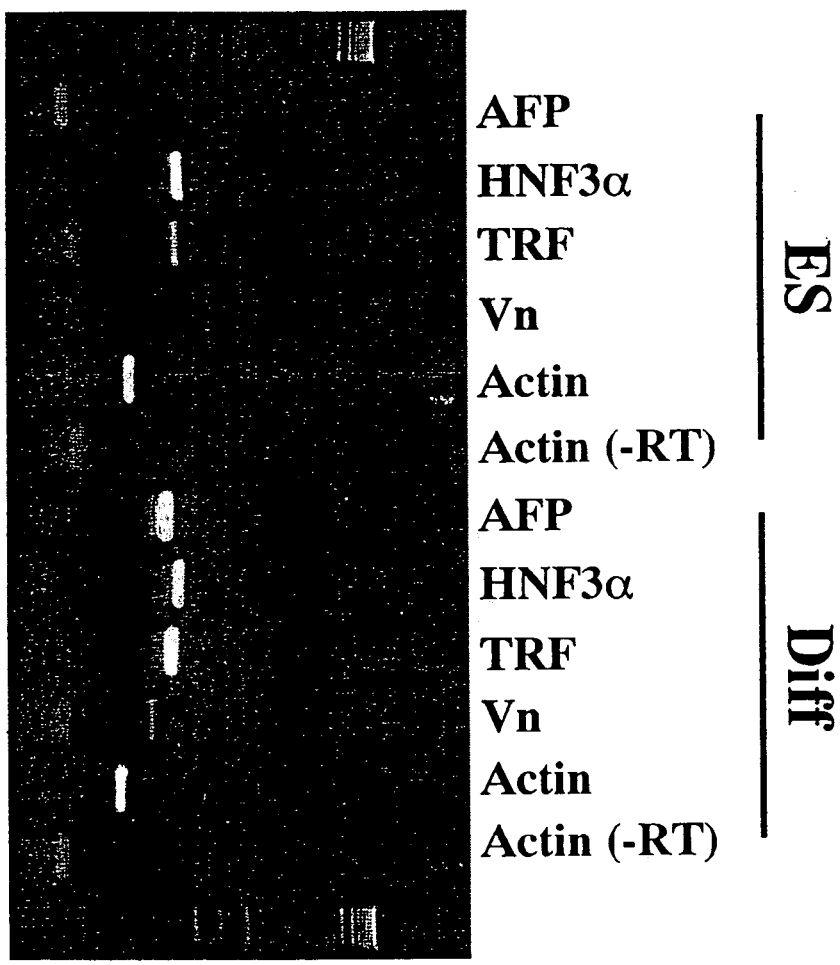

FIG. 4 shows agarose gel electrophoresis of RT-PCR analysis for markers of endodermal lineages obtained from stem cells or spontaneously differentiating ES cells. Markers include alphafetoprotein, HNF3 alpha, transferrin, vitronectin. Actin is shown to indicate RNA quantity.

Figure 5:
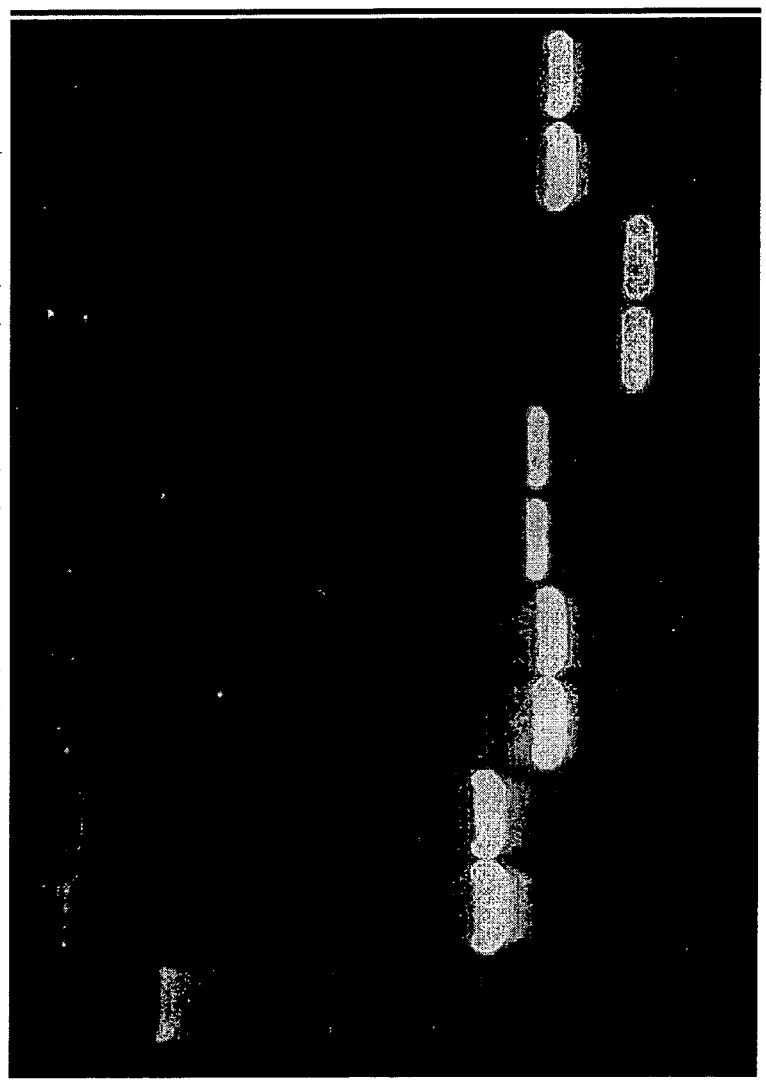

FIG. 5 shows RT-PCR analysis of expression of BMP-2 and its receptor subunits in cultures of ES cells. For each pair of products, left hand lane shows control and right differentiated culture. Lanes: molecular weight marker, BMP-2 BMPR1a, BMPR2 beta actin, and activin receptor beta.

Figure 6:
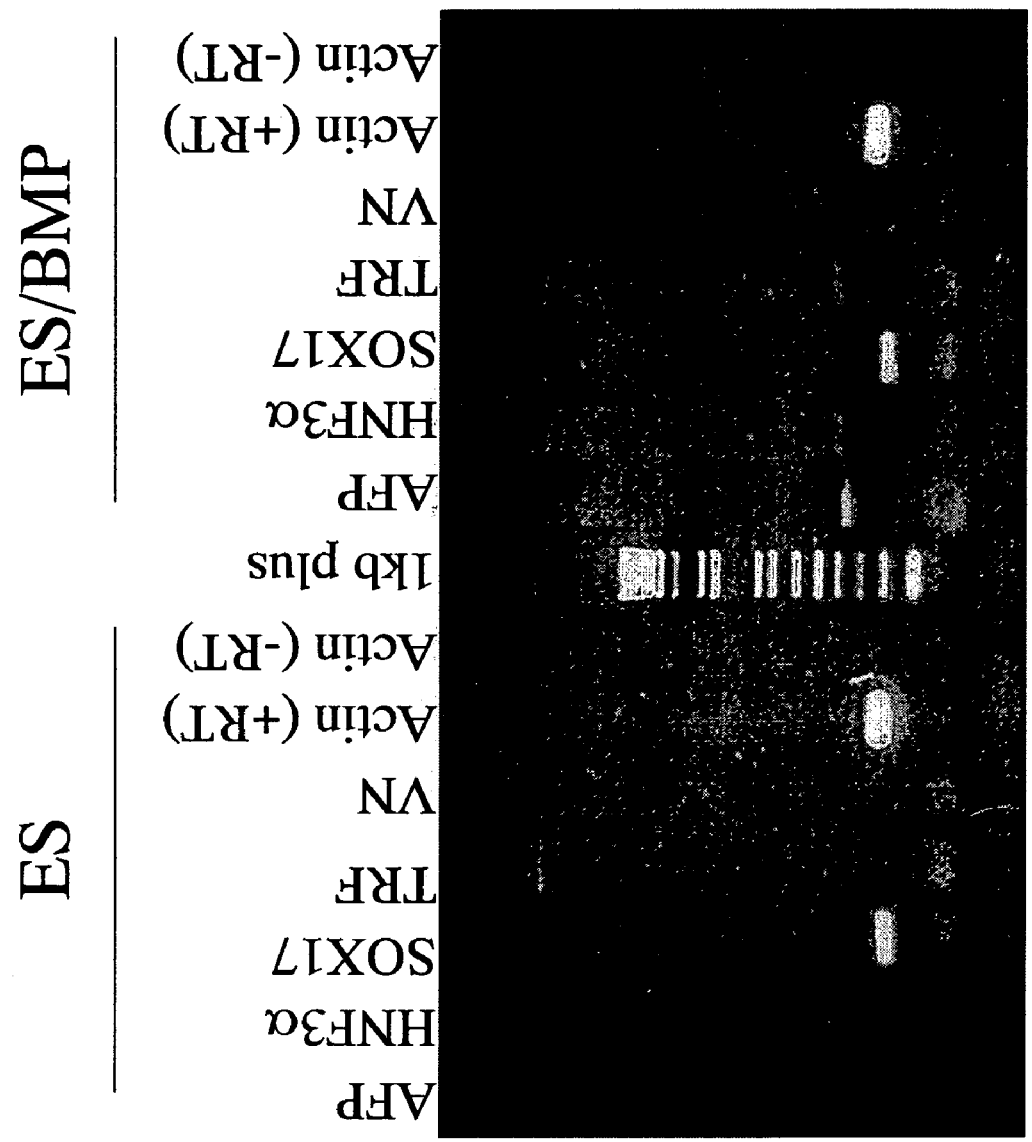

FIG. 6 shows RT-PCR analysis of the effect of BMP-2 treatment of human ES cells on their expression of stem cell and endodermal markers. Left hand side, control, right hand side BMP-2 treated. Shown are products representing transcripts for alphafetoprotein, hepatic nuclear factor 3 alpha, Sox 17, transferrin, vitronectin, beta actin, and beta actin no RT control.

Figure 7A:
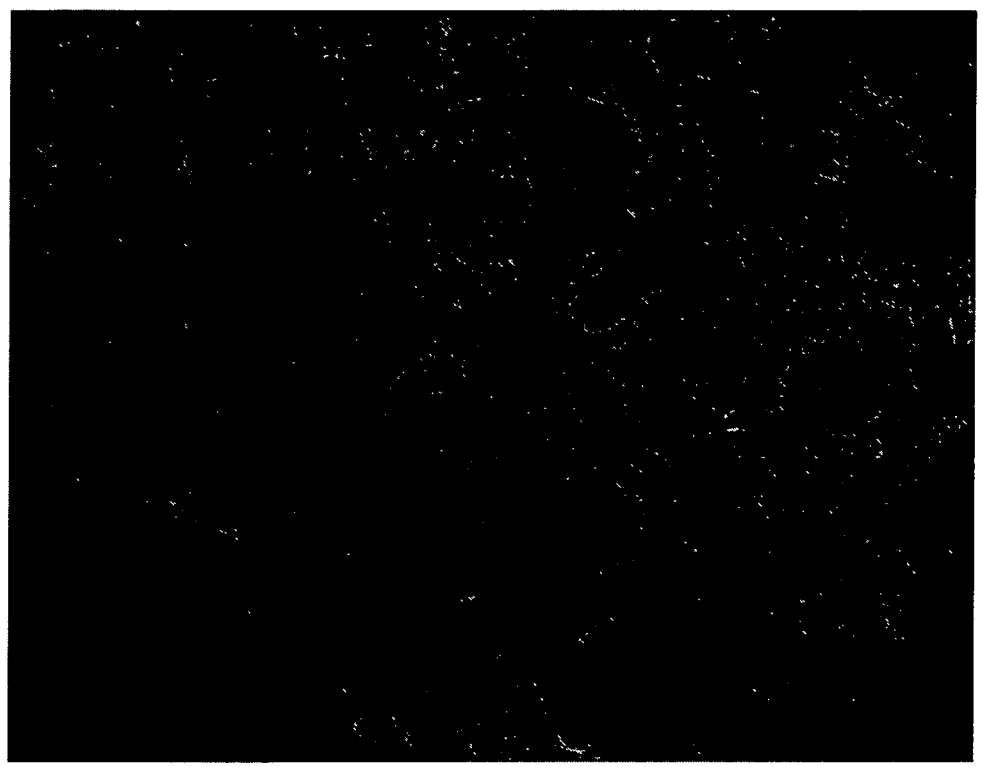
Figure 7B:
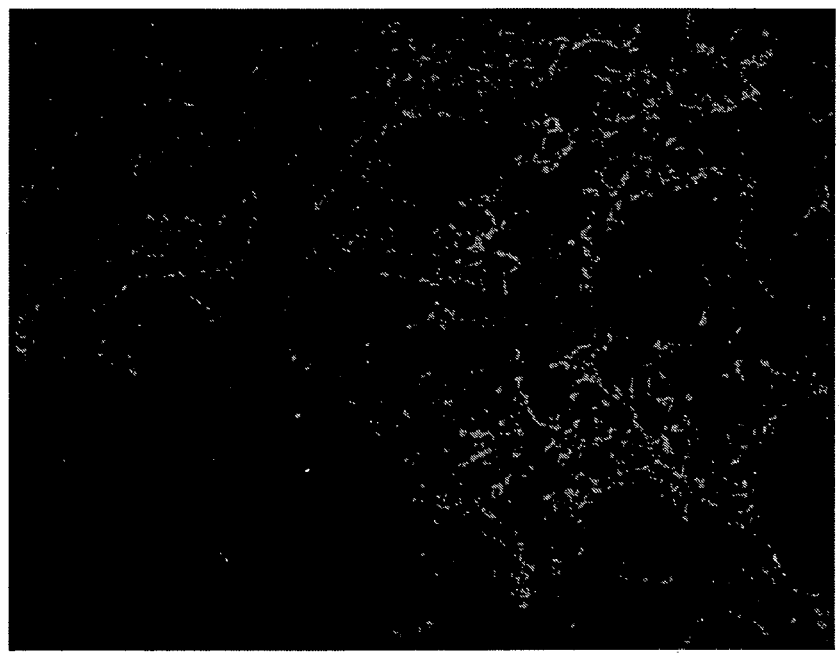

FIG. 7 shows immunochemical analysis of the expression of low molecular weight cytokeratins A (FIG. 7A) and the extracellular matrix protein laminin in human ES cells treated with BMP-2 (FIG. 7B).

Figure 8:

FIG. 8 shows phase contrast micrographs of control (A) and noggin treated ES cells (B).

Figure 9:

FIG. 9 shows effect of noggin treatment on the proportion of human ES cells expressing the stem cell marker GCTM-2. Blocking antibody against gp-130 has no effect on ES differentiation, indicating a lack of response of human ES cells to stimulation of this receptor.

Figure 10:
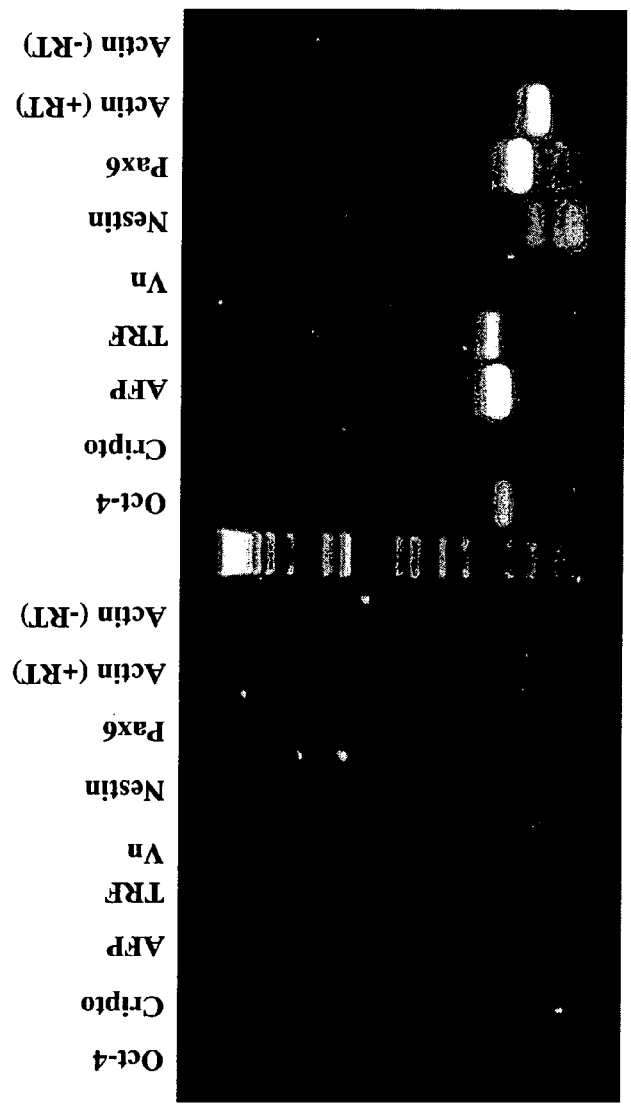

FIG. 10 shows RT-PCR analysis of gene expression in control and noggin treated ES cell cultures. Left, Noggin treated cells; right, control ES cells. RT-PCR products representing cDNA for October-4, Cripto, alphafetoprotein, transferrin, vitronectin, nestin, Pax-6, beta actin, and no RT control for beta actin are shown. October-4 and Cripto are stem cell markers, alphafetoprotein, transferrin, and vitronectin are extraembryonic endoderm markers, and nestin and Pax-6 are markers of early neuroectoderm. The ES control culture has begun to differentiate and therefore lacks the Cripto transcript but expresses alphafetoprotein and transferrin as well as nestin and Pax-6.

Figure 11:

FIG. 11 shows phase contrast image of a neurosphere derived from noggin treated ES cell cultures.

Figure 12:
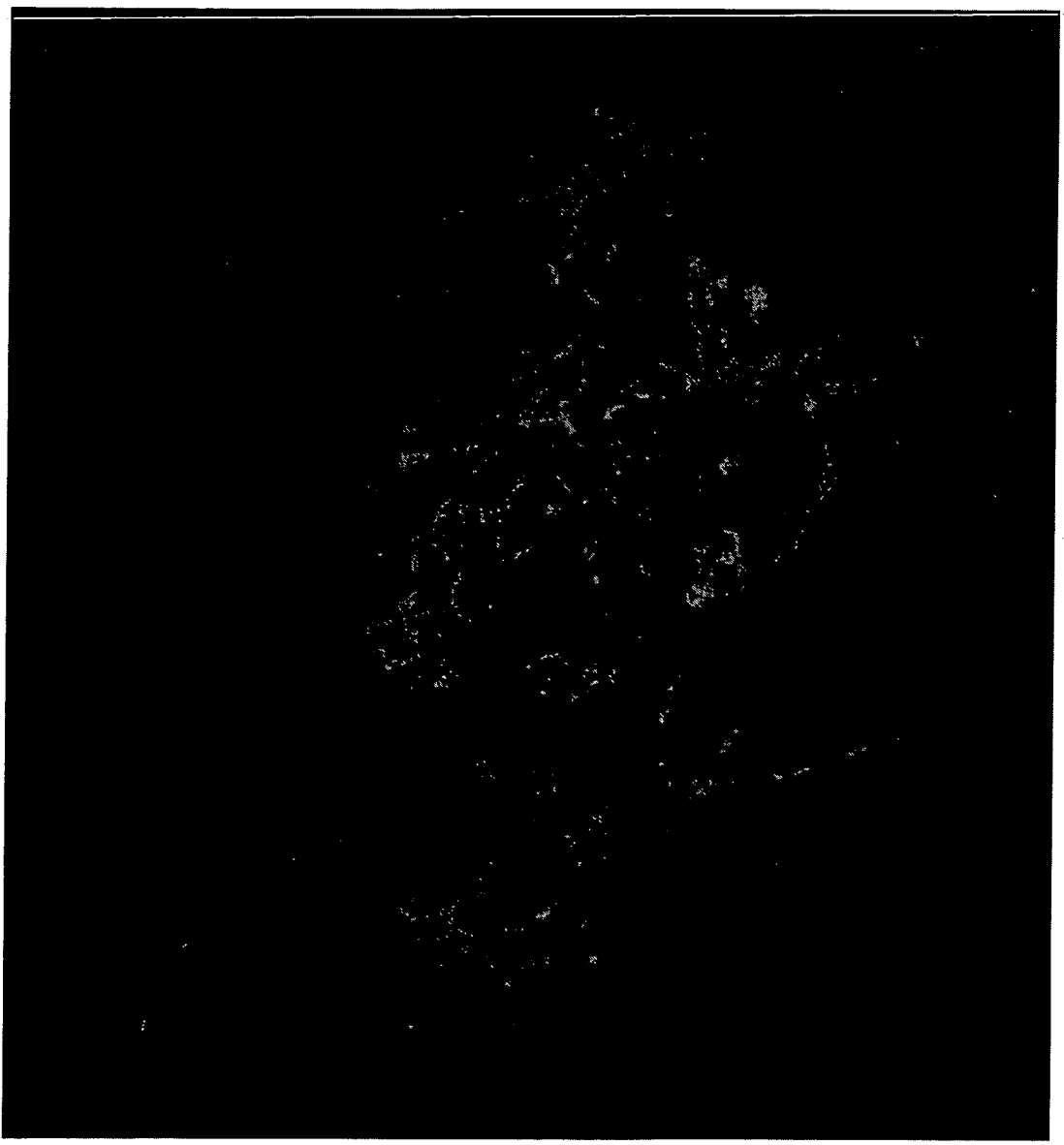

FIG. 12 shows fluorescence micrograph of noggin treated cells stained with an antibody against 68 kDa neurofilament protein.

DESCRIPTION OF THE INVENTION

In a first aspect of the present invention there is provided a preparation of undifferentiated embryonic stem cells sustainable for a prolonged period in an undifferentiated state which favour enhanced stem cell renewal and preferably somatic differentiation. Preferably the cells are capable of somatic differentiation in vitro and are inclined to differentiate away from an extraembryonic lineage.

Embryonic stem cells have a natural capacity to differentiate into cells resembling those of extraembryonic endodermal lineages in the early human embryo. Accordingly, if the cells are not treated to prevent this defaulted differentiation pathway, somatic lineages cannot be effectively attained or maintained in vitro for further studies or manipulation. It is desired to maintain the cells in an undifferentiated state giving greater capacity for manipulation of differentiation particularly into somatic lineages.

The purified preparation of the present invention is capable of prolonged cultivation and are substantially maintained under conditions which do not induce cell death or differentiation. However, it is preferable that the cells are capable of differentiation particularly toward somatic lineages such as when a differentiating signal, is introduced.

Preferably, the embryonic cells are capable of maintaining an undifferentiated state when cultured on a fibroblast feeder layer generally under non-differentiating conditions. Desirably the fibroblast feeder layer does not induce cell death or extraembryonic differentiation.

The cultured cells maintained in the undifferentiated state may have the potential to differentiate in vitro when subjected to differentiating conditions. However when a differentiation signal is given it is best that the cells have the capacity to differentiate in vitro into a wide array of somatic lineages.

The promotion of stem cells capable of being maintained in an undifferentiated state in vitro on one hand, and which are capable of differentiation in vitro into somatic lineages on the other hand, allows for the study of the cellular and molecular biology of early human development, functional genomics, generation of differentiated cells from the stem cells for use in transplantation or drug screening and drug discovery in vitro.

Once the cells are maintained in the undifferentiated state, they may be differentiated to mature functional cells. The embryonic stem cells are derived from the embryo and are pluripotent and have the capability of developing into any organ or tissue type such as blood cells, neuron cells or muscle cells.

In another aspect of the present invention, there is provided a method of culturing undifferentiated embryonic stem cells, said method including:

obtaining a source of undifferentiated embryonic stem cells; and culturing the embryonic stem cells in the presence of an indirect or direct antagonist of a BMP-mediated default pathway of extra embryonic endoderm differentiation.

Applicants have found that the default pathway of extraembryonic endoderm differentiation seen in ES cell cultures grown under standard conditions may be mediated by endogenous production of the growth and differentiation factor BMP (bone morphogenetic protein), a member of the transforming growth factor beta superfamily. Untreated cultures of ES cells grown under standard conditions express transcripts for both BMP and its receptors. Moreover, cultures treated with BMP will undergo differentiation into a cell type with a morphology similar to the flat squamous cells found in spontaneously differentiating cultures, and will express immunochemical markers and genes characteristic of this cell type. It is therefore posulated by the applicants that a BMP mediated autocrine loop driving extraembryonic endoderm differentiation in human ES cell cultures may lead to extinction of stem cells (undifferentiated) or inhibition of production of desired somatic types.

The undifferentiated embryonic stem cells of the present invention may be obtained by any means available to the skilled addressee. However, they may be obtained by the methods outlined in PCT/AU99/00990. The entire contents of that application are incorporated herein.

The BMPs are multifunctional cytokines and members of the TGFβ superfamily. They are regulated by BMP binding proteins such as noggin and chordin. Several BMPs exist having various functions. For instance, BMP-2 is involved in regulating bone formation whilst BMP-4 has been implicated in development as a regulator of mesodermal induction.

The BMP-mediated default pathway is mediated by expression of BMP as measured by expression of BMP and its receptors. Preferably, it is measured by expression of BMP-2 and its receptors.

In a preferred embodiment, the present invention provides a method of culturing undifferentiated embryonic stem cells, said method including:

obtaining a source of undifferentiated embryonic stem cells; and culturing the embryonic stem cells in the presence of an indirect or direct antagonist of a BMP-2 mediated default pathway of extraembryonic endoderm differentiation.

This was a surprising result since BMP-2 is implicated in bone formation and not involved in the enhancement of stem cell renewal or favouring somatic differentiation.

A number of naturally occurring indirect or direct antagonists of BMPs have been identified. Direct antagonists of BMPs maybe selected from the group including, but not restricted to fetuin, noggin, chordin, gremlin, follistatin, cerberus, DAN, or the ectodomain of BMPR1A (a BMP receptor protein). Preferably the BMP-2 antagonist is noggin.

An indirect BMP antagonist is one which does not act directly on BMP but has an effect on other factors which influence BMP. Preferably an indirect BMP antagonist is insulin or insulin analogue.

Insulin or insulin analogues and homologues may antagonise BMP indirectly, by blocking a stress response of human ES cells. Conditions which place stress on stem cells may lead to this default form of differentiation toward extraembryonic endoderm differentiation.

Accordingly, in a preferred embodiment of the present invention, there is provided a method of culturing undifferentiated embryonic stem cells, said method including:

obtaining a source of undifferentiated embryonic stem cells; and culturing the embryonic stem cells in the presence of noggin.

Any source of the BMP antagonist may be used. However, a mouse BMP antagonist noggin has been found by the applicants to be particularly effective in preventing extraembryonic differentiation. Applicants have found a mouse BMP noggin consisting of a signal peptide, the mouse noggin peptide from amino acid residues 20 to 232, a peptide linker, and the Fc region of human IgGI (R&D Systems) maybe used to maintain the culture of undifferentiated embryonic stem cells. However, other sources of noggin and the peptide sequence may be used in these dimensions to prevent extraembryonic differentiation and preferably drive the ES cells in a desired direction either to somatic differentiation or to ES cell renewal.

A preferred range of BMP antagonist is in the range of 100–500 ng/ml to cells grown under standard ES cell culture conditions. This range is particularly effective for noggin.

The BMP antagonist may be added to an undifferentiated ES cell culture at any stage. However, it is preferred that the antagonist is added before the default pathway of extraembryonic endoderm differentiation begins.

The BMP antagonist may be cultured with the cells for any period, preferably for a period sufficient to obtain a homogeneous population.

In another aspect of the present invention, there is provided a method of producing a progenitor cell from an ES cell, said method comprising:

obtaining a source of undifferentiated embryonic stem cells; and culturing the embryonic stem cells in the presence of an antagonist of a BMP mediated default pathway of extra embryonic endoderm differentiation for a period sufficient to differentiate the ES cell to a progenitor cell.

Preferably the antagonist is any antagonist alone or in combination as listed above. More preferably, it is an antagonist of a BMP-2 mediated default pathway. Noggin is mostly preferred.

The period sufficient to differentiate the ES cell will depend on the antagonist used. Where noggin is used, a period of at least 5 days may provide progenitor cells differing in appearance to ES cells.

Applicants have found that after approximately 5 days noggin treated cultures (100–500 ng/ml) consisted of colonies of distinct small round cells differing in appearance from ES cells. In contrast to control cultures, colonies in noggin treated dishes contained no flat squamous epithelial cells or cystic structures similar to those in BMP-2 treated cultures. The growth of the colonies was also inhibited in the presence of noggin, and the proportion of cells bearing the stem cell marker GCTM-2 was reduced compared to control cultures. The noggin cultures become homogenous in appearance, though at later time points they may show a tendency to form palisade cell structures.

The immunophenotype of the noggin treated cells may be distinguished by their lack of expression of a number of markers characteristic of ES cells or differentiated cells found spontaneously at early time points at approximately 7–10 days following ES cell subculture under standard conditions. Thus the noggin induced cells maybe characterised by being unreactive with any one of following antibodies including PHM4 recognising MHC Class 1 surface molecules, anti-desmin, UJ13A reactive with polysialylated N-CAM, Cam 5.2 reactive with low molecular weight cytokeratins, AMF reactive with vimentin intermediate filaments, antibody to 160 kDa neurofilament protein, GCTM-2 reactive with a proteoglycan present on the surface of ES cells, TG42.1 reactive with a 25 kDa protein which copurifies with the proteoglycan recognised by GCTM-2 and is found on stem cells and other cell types, monoclonal antibody 5G7 reactive with an unknown molecule present on a small proportion of cells in spontaneously differentiating human EC cell cultures, and monoclonal antibodies BH6N and bTAN 20 reactive with human Notch 1 and Notch 2. However, a significant proportion of cells present in noggin treated cultures may be reactive with an antibody recognising the 68 kDa neurofilament protein.

The noggin treated cells may be further characterised in biological assays. Addition of 25 ng/ml recombinant human BMP-2 along with 250 ng/ml noggin has been found by the Applications to lead to the appearance of squamous cells and cysts characteristic of spontaneously differentiating ES cell cultures or BMP-2 treated cultures, indicating that BMP-2 could antagonise the noggin effect. The noggin treated cells could be subcultivated under standard conditions for ES cell culture and retain their distinctive morphology under these conditions.

In yet another aspect of the present invention there is provided a method of producing a somatic cell from an ES cell, said method comprising:

obtaining a source of undifferentiated embryonic stem cells;

culturing the embryonic stem cells in the presence of an antagonist of a BMP mediated default pathway of extra embryonic endoderm differentiation for a period sufficient to differentiate the ES cell to a progenitor cell;

obtaining a progenitor culture medium derived from another culture of a somatic progenitor;

culturing the progenitor cell in the progenitor culture medium; and obtaining a somatic cell from a lineage of the somatic progenitor.

The somatic cell may be any cell of the somatic lineage. The use of the BMP antagonist can produce a progenitor cell which is capable of differentiation into any somatic lineage.

The progenitor culture medium may be derived from the culture of a somatic progenitor which also can differentiate into the desired somatic cell. Preferably, for a neural cell, it is desired that the progenitor culture medium is derived from a culture of a neural progenitor. Hence, the somatic cell (preferably neural cell) which is differentiated via the route described will have a lineage of the somatic progenitor (neural progenitor).

The BMP antagonists are as described above. Preferably, the antagonist is noggin.

Applicants have found that if the noggin treated cells were placed in neural progenitor culture medium, they formed structures with the appearance of neurospheres which could be maintained for at least two weeks in culture. This finding, along with the presence of cells expressing the 68 kDa neurofilament protein in noggin treated cultures, suggests that the noggin cells are capable of undergoing commitment of neurogenic lineages, in line with effects of noggin in early verterate embryos.

Accordingly, an antagonist of BMP-2 may alter the outcome of differentiation of human ES cells.

Accordingly in a preferred aspect of this invention there is provided a method of producing a cell of a neurogenic lineage, said method comprising:

obtaining a source of undifferentiated embryonic stem cells;

culturing the embryonic stem cells in the presence of noggin to produce a progenitor cell;

obtaining a neural progenitor culture medium derived from another culture of a neural progenitor; and culturing the progenitor cell in the neural progenitor culture medium for a period sufficient to obtain a cell of a neurogenic lineage.

The period to culture the progenitor cell may be dependent upon the progenitor culture medium. However, the period may be determined when a substantially homogeneous cell population is obtained.

In another aspect of the present invention there is provided a population of stem cells or progenitor cells identified by particular patterns of surface antigen expression, including but not limited to, a lack of expression of ES cell markers such as GCTM-2 and surface antigen expression by lack of reaction to any of the following antibodies including PHM4 recognising MHC Class 1 surface molecules, anti-desmin, UJ13A reactive with polysialylated N-CAM, Cam 5.2 reactive with low molecular weight cytokeratins, AMF reactive with vimentin intermediate fiaments, antibody to 160 kDa neurofilament protein, GCTM-2 reactive with a proteoglycan present on the surface of ES cells, TG42.1 reactive with a 25 kDa protein which copurifies with a proteoglycan recognised by GCTM-2 and is found on stem cells and other cell types, monoclonal antibody 5G7 reactive with an unknown molecule present on a small proportion of cells in spontaneously differentiating human EC cell cultures, and monoclonal antibodies BH6N and bTAN 20 reactive with human Notch 1 and Notch 2.

In a further preferred aspect, the cells are reactive with an antibody which recognises a 68 kDa neurofilament protein.

In another preferred embodiment of the present invention there is provided a method of culturing undifferentiated embryonic stem cells, said method including:

obtaining a source of undifferentiated embryonic stem cells; and culturing the embryonic stem cells in the presence of a cell derived insulin or insulin analogue induced factor.

Preferably the cells deriving the factor are fibroblasts or cultures containing embryonic stem cells.

In another preferred embodiment of the present invention there is provided a method of culturing undifferentiated embryonic stem cells, said method including:

obtaining a source of undifferentiated embryonic stem cells; and culturing the embryonic stem cells in the presence of insulin or an insulin analogue.

In yet another preferred embodiment of the present invention there is provided a method of culturing undifferentiated embryonic stem cells, said method including:

obtaining a source of undifferentiated embryonic stem cells; and culturing the embryonic stem cells in the presence of a fibroblast feeder layer and insulin or an insulin analogue.

Accordingly, this embodiment of the invention provides a method of culturing embryonic stem cells so as to enhance stem cell survival and growth during routine culture and to enhance the extent and variety of somatic cells obtained under differentiation conditions. Insulin and Insulin analogues may have an indirect antagonistic effect on the BMP mediated default pathway.

In a further preferred embodiment of the invention, there is provided a method of culturing undifferentiated embryonic stem cells, said method including:

obtaining a source of undifferentiated embryonic stem cells;

culturing the embryonic stem cells on a fibroblast feeder cell layer; and subjecting the cultured cells to an effective amount of insulin or an insulin analogue.

The cells may be cultured on fibroblast cells and then subjected to insulin or an insulin analogue possibly after the cells have been initially cultured for a time to establish the ES cell culture.

The Applicants have found a means to achieve this by culturing the embryonic stem cells generally on a fibroblast feeder cell layer in the presence of insulin or an insulin analogue. The analogue may be IGF-1 or IGF-2.

Preferably the insulin analogue is IGF-2. The insulin or an analogue may induce the fibroblasts or the stem cells to produce a factor(s) capable of supporting stem cell growth and which favours somatic differentiation.

Insulin or analogues thereof including IGF-1 or IGF-2 have been used to support the growth and survival of a wide range of cultured mammalian cells.

However, the positive effects of insulin or analogues thereof including IGF-1 or IGF-2 on growth and survival of embryonic stem cells cultured in the presence of serum and in the presence or absence of a feeder cell support have not been reported.

The action of insulin or an insulin analogue such as IGF-2 may be directly on the embryonic stem cells, or indirectly through the action of insulin or an analogue on a feeder cell layer (if present) or by a combination of these two mechanisms. Insulin or an analogue may function in combination with factors produced by the fibroblasts, or by stem cells themselves, such as Cripto or GDF-3.

For instance, where the embryonic stem cells are grown in the absence of a feeder cell layer, the cell derived insulin or insulin analogue induced factor may be harvested from a separate culture of cells such as fibroblasts exposed to insulin or insulin analogue. The conditioned medium derived from this source containing the insulin or insulin analogue induced factor may then be introduced to the ES culture at a concentration suitable to maintain the cells in an undifferentiated state but capable of differentiation into a somatic lineage. Alternatively, the ES cells may be grown on a fibroblast feeder cell layer and the insulin or insulin analogue may act on the ES cells themselves, in conjunction with factors produced by the fibroblasts or by the stem cells themselves. The growth factors GDF-3 and cripto are produced by human ES cells. Addition of these factors along with insulin or insulin analogue may further enhance cell growth. Other factors may be produced by insulin or insulin analogue treated stem cells which will enhance stem cell growth or survival.

Insulin or an insulin analogue such as IGF-2 may be added at a concentration of approximately 10 ng/ml to 10 µg/ml to the fibroblast culture from which the factor is liberated and preferably harvested. It may also be added to an ES cell culture maintained on a fibroblast feeder cell layer which liberates the factor in situ for immediate benefit, or to act on the ES cells directly. Ideally, the concentration is 10 μg/ml.

The insulin or an analogue may be added at the time of cultivation either directly to the ES cells on the fibroblast feeder cell layer or to a fibroblast culture from which the conditioned medium is harvested or during a process of obtaining the ES cells. The insulin or an analogue may be added alone or in combination with other factors such as GDF-3 or Cripto.

In another aspect of the present invention, there is provided a cell derived insulin or insulin analogue induced factor capable of maintaining ES cells in an undifferentiated state but capable of differentiation into a somatic lineage. Preferably the factor is induced by subjecting fibroblasts or embryonic stem cells to insulin or analogues thereof. The factor is generally found in the culture medium (supernatant) of fibroblasts or embryonic stem cells and may be isolated therefrom.

The cell derived insulin or insulin analogue induced factor from fibroblasts may be identified by the following:

1) Treating a feeder cell layer with insulin or an analogue, harvesting conditioned medium from treated or control cells, testing the biological effects of these media on ES cells, and identifying the active factors by biochemical means known to the skilled addressee such as by chromatography by testing each factor; or 2) Differential analysis of gene expression in control cells such as fibroblasts and fibroblasts treated with insulin or analogue to identify these factors using for example representation of display analysis followed by standard techniques of molecular cloning and recombinant protein expression, or related techniques known to the skilled addressee.

Likewise, ES derived insulin or insulin analogue induced factors might be identified by the following:

1) Treating the ES cells with insulin or an analogue, harvesting conditioned medium from treated or control cells, testing the biological effects of these media on ES cells, and identifying the active factors by biochemical means known to the skilled addressee such as by chromatography by testing each factor; or 2) Differential analysis of gene expression in control ES cells and ES cells treated with insulin or an analogue to identify these factors using for example representational display analysis followed by standard techniques of molecular cloning and recombinant protein expression, or related techniques known to the skilled addressee.

The ES cells may be grown in the presence or absence of a feeder cell layer. Where a feeder cell layer is used, it is preferably a fibroblast feeder cell layer of the type described in PCT/AU99/00990. The entire contents of that application are incorporated herein.

The effects of insulin or an analogue on the fibroblast derived insulin induced factor may be evident within 5 to 7 days of subcultivation of an ES colony in media containing insulin.

In another aspect of this invention there is provided populations of stem cells or committed progenitor cells identified by particular patterns of surface antigen expression, including but not limited to those which are positive for both GCTM-2 and TRA 1-60, those which are positive for one or other of these antigens, and those which lack either antigen on their surface The effect of insulin or analogue or the insulin or insulin analogue induced factor is evidenced morphologically by a more tightly packed and uniform appearance compared to colonies grown in the absence of insulin or analogues or the factor. Many more cells of uniform stem cell morphology are present in treated colonies, and immunostaining methods using stem cell specific markers to count the number of cells expressing such markers or estimating their proportion by flow cytometry using such stem cell specific markers may be used to confirm this. Without being limited by theory, it is considered that the chief effect of insulin or analogue treatment or the effect of the factor over the short term is to increase the number of cells in each colony without a marked effect on the proportion of stem cells present, consistent with an effect on stem cell multiplication or survival.

Applicants have observed that there is heterogeneity even in cultures consisting of cells with the appearance of stem cells. For example, the proportion of cells reactive with the markers GCTM-2 is consistently lower than that of cells reacting with TRA 1-60. This may reflect stem cells at different levels of maturation within the population. Insulin or analogue treatment consistently produces a modest decrease in the proportion of TRA 1-60 positive cells but does not change the proportion of GCTM-2 positive cells. This may be indicative of a change in the rate of stem cell maturation. Isolation of the various subpopulations of cells (eg TRA1-60+GCTM-2+, GCTM-2+TRA1-60−, TRA 1-60+GCTM-2−, or TRA 1-60−GCTM-2−) in control and insulin or analogue treated cultures may help identify novel cellular intermediates with desired properties, such as enhanced colony forming ability or somatic differentiation capacity.

It has now been found that stem cells grown in the presence of insulin or analogue or the insulin or analogue induced factor persist much longer than stem cells grown in the absence of insulin or analogue or of the factor. They may still be present up to 3 weeks or more whilst control colonies (grown in the absence of insulin or the factor) will consist of differentiated cells.

Undifferentiated stem cells may be propagated and subcultured for multiple passages in the presence of insulin or analogue or the factor. Successful long term maintenance of stem cells in the presence of insulin or analogue or the factor may be proven by the continued presence in the cultures of diploid cells bearing stem cell markers and expressing stem cell specific genes such as October-4. Furthermore, in cultures passaged through 20 to 30 population doublings, stem cells may be demonstrated by such cells forming teratomas in SCID mice which contain derivatives of all three embryonic germ layers.

Hence insulin or an analogue or the cell derived insulin or insulin analogue induced factor is useful as described in the present invention to increase the number and persistence of stem cells during routine passage.

In another aspect of the present invention there is provided a method of culturing undifferentiated embryonic stem cells capable of somatic differentiation in vitro, said method including:

obtaining a source of undifferentiated embryonic stem cells; and culturing the embryonic stem cells in the presence of a cell derived insulin or insulin analogue induced factor.

Preferably the cells deriving the factor are fibroblasts or embryonic stem cells.

In another aspect of the present invention there is provided a method of culturing undifferentiated embryonic stem cells capable of somatic differentiation in vitro, said method including:

obtaining a source of undifferentiated embryonic stem cells; and culturing the embryonic stem cells in the presence of fibroblast cells and insulin or an insulin analogue.

In another aspect of the present invention there is provided a method of culturing undifferentiated embryonic stem cells capable of somatic differentiation in vitro, said method including:

obtaining a source of undifferentiated embryonic stem cells; and culturing the embryonic stem cells in the presence of insulin or an insulin analogue.

In addition to affecting the number and persistence of stem cells during routine passage, the addition of insulin or analogue or the factor can also affect the outcome of differentiation.

In a preferred aspect of the invention, there is provided a method of culturing undifferentiated embryonic stem cells capable of somatic differentiation in vitro, said method including:

obtaining a source of undifferentiated embryonic stem cells;

culturing the embryonic stem cells on a fibroblast feeder cell layer; and subjecting the cultured cells to an effective amount of insulin or an insulin analogue.

The cells may be cultured on fibroblast cells and then subjected to insulin or an insulin analogue possibly after the cells have been initially cultured for a time to establish the ES cell culture.

Somatic differentiation is favoured under conditions that limit stem cell renewal but support cell survival and limit extraembryonic differentiation. Applicants have found that addition of insulin to fibroblast feeder cells limits extraembryonic differentiation into the extraembryonic endodermal cell type. The decreased proportion of cells undergoing extraembryonic differentiation may be demonstrated by the lower proportion of cells bearing characteristic markers of this lineage. The phenotypic identification of the extra embryonic cell may be demonstrated by the presence of specific markers of the extraembryonic endodermal lineage, using immunocytochemistry or RT-PCR, such markers including transcription factors such as HNF3 alpha and beta, cytokeratins including cytokeratin 19, the cell adhesion molecule vitronectin and basement membrane molecules such as Type IV collagen and laminin. Stem cells persist longer in cultures treated with insulin or an analogue thereof or the fibroblast derived insulin or insulin analogue induced factor and as such cultures may be maintained without renewal of a feeder layer, somatic differentiation is strongly favoured, with neuroectoderm precursors (staining for N-CAM and nestin and expressing Pax-6) appearing first, in larger numbers than in control dishes. Thereafter, many additional cell types may be seen in insulin or insulin-induced factor treated cultures that are not usually detected in control cultures due to high proportions of extraembryonic cells in the latter. These novel cell types may be characterised by distinctive morphology and patterns of gene expression.

In yet another preferred embodiment of the present invention there is provided a method of culturing undifferentiated embryonic stem cells, said method including:

obtaining a source of undifferentiated embryonic stem cells; and culturing the embryonic stem cells in the presence of an antagonist of a BMP mediated default pathway of extraembryonic endoderm differentiation and a cell derived insulin or insulin analogue induced factor.

In another preferred embodiment of the present invention, there is provided a method of culturing undifferentiated embryonic stem cells, said method including:

obtaining a source of undifferentiated embryonic stem cells; and culturing the embryonic stem cells in the presence of an antagonist of a BMP mediated default pathway of extraembryonic endoderm differentiation and fibroblast cells and insulin or insulin analogue.

In another preferred embodiment of the present invention, there is provided a method of culturing undifferentiated embryonic stem cells, said method including obtaining a source of undifferentiated embryonic stem cells; and culturing the embryonic stem cells in the presence of an antagonist of a BMP mediated default pathway of extraembryonic endoderm differentiation and insulin or insulin analogue.

The use of a BMP-antagonist and insulin or insulin analogues is as described above but may be used in combination to antagonize the BMP-mediated default pathway toward extra embryonic endoderm differentiation. Preferably, the BMP-antagonist is a noggin.

The cell lines produced in the presence of an antagonist of a BMP-mediated default pathway and insulin or insulin analogue induced factors as described herein, particularly favour embryonic stem cell renewal.

In another preferred embodiment, the undifferentiated cells cultured according to the invention differentiate under differentiating conditions in vitro to form somatic lineages when subject to a differentiation signal.

In another aspect there is provided a differentiated committed progenitor cell line capable of differentiation into somatic cells, preferably produced by the methods described herein.

In another aspect, there is provided a somatic cell capable of differentiation in vitro from an undifferentiated embryonic stem cell. There is also provided a committed somatic cell capable of giving rise to mature somatic cells. The cells may differentiate into embryonic mesoderm and embryonic endoderm lineages, including, but not limited to cartilage, muscle, bone, hepatocyte, pancreatic islet cells and respiratory endothelium. Preferably the somatic cells are derived from any of the methods described herein.

These cells may be obtained by somatic differentiation of human ES cells, identified by markers. These cells may be isolated in pure form from differentiating ES cells, in vitro, and propagated in vitro. They may be induced to undergo differentiation to mature somatic cell lineages.

In the presence of a differentiation signal, undifferentiated ES cells in the right conditions will differentiate into derivatives of the embryonic germ layers (endoderm, mesoderm and ectoderm), and/or extraembryonic tissues such as neuron tissue. This differentiation process can be controlled.

Conditions for obtaining differentiated cultures of somatic cells from embryonic stem cells are described in PCT/AU99/00990, the contents of which are incorporated herein.

Once the cells have been induced to differentiate, the various cell types, identified by means described above, may be separated and selectively cultivated. The progenitor cells may differentiate into any cells including embryonic mesoderm and embryonic endoderm lineages, including, but not limited to cartilage, muscle, bone, hepatocyte, pancreatic islet cells and respiratory endothelium.

The present invention will now be more fully described with reference to the following examples. It should be understood, however, that the description following is illustrative only and should not be taken in any was as a restriction on the generality of the invention described above.

EXAMPLES

Example 1

Action of Insulin on Short Term Maintenance of Human Embryonic Stem Cells

Figure 1A:
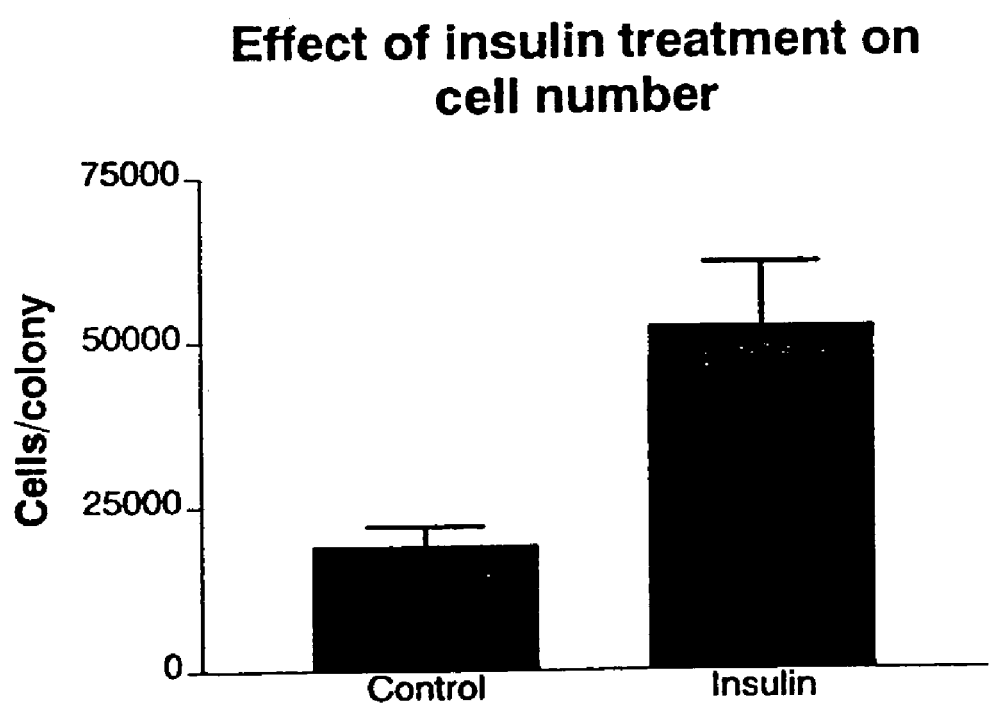
FIG. 1A shows a graph of the number of cells/colony obtained when ES cells are cultivated under control conditions or in the presence of insulin for 7 days. The percentage of cells reactive with stem cell markers TRA-1-60 and GCTM-2 is shown in FIG. 1B.
Figure 1B:
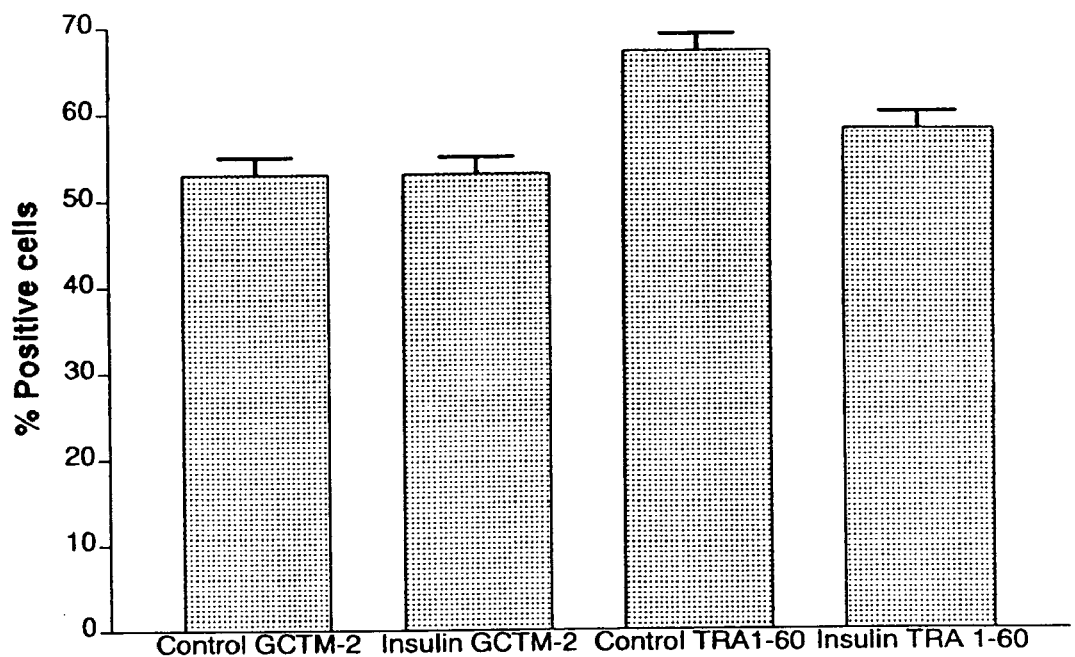
Figure 2:
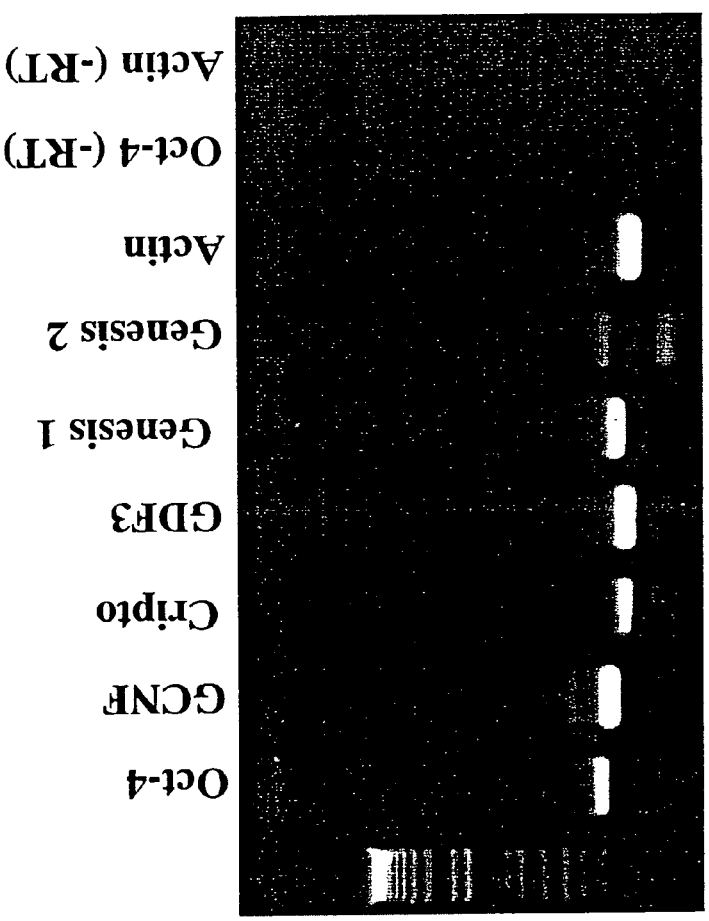
FIG. 2 shows agarose gel electrophoresis analysis of RT-PCR for October-4, GCNF, cripto, GDF-3, genesis, and P actin on control ES cell cultures (A) ES cell cultures maintained in insulin for five passages.
Figure 3A:
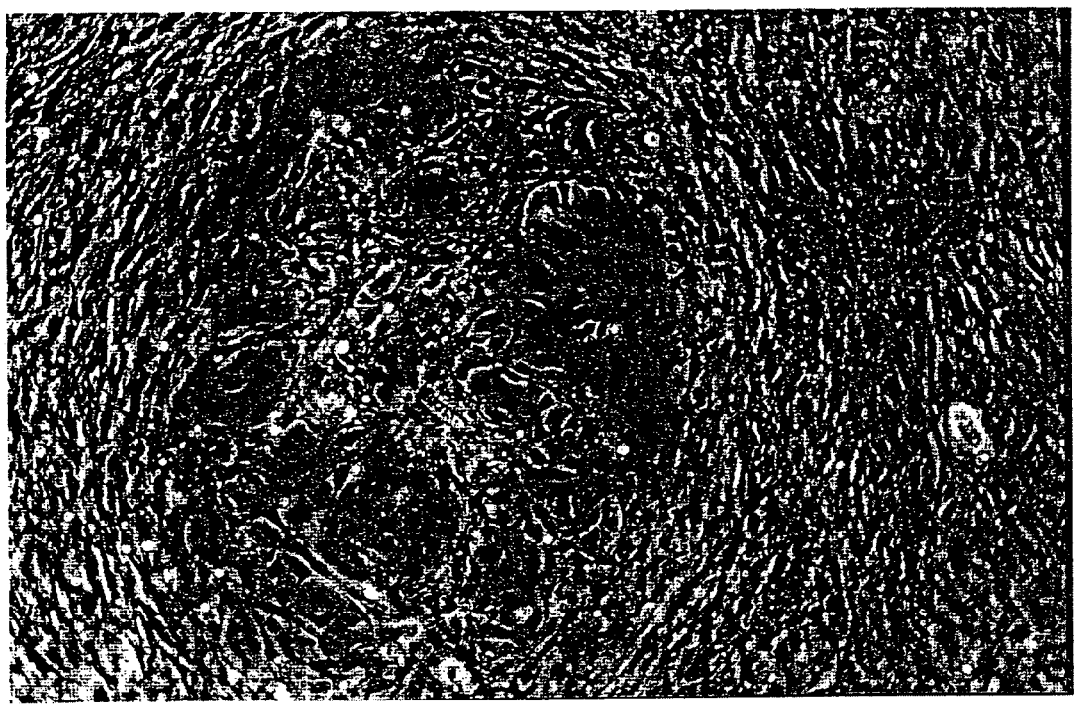
FIG. 3 shows phase contrast morphology of differentiating ES cell cultures grown in control medium (A) or in the presence of insulin (B–D). Control cultures consist mainly of squamous epithelial cells which form cysts, while insulin tested cultures retain a range of cell types.
Figure 3B:
Figure 3C:
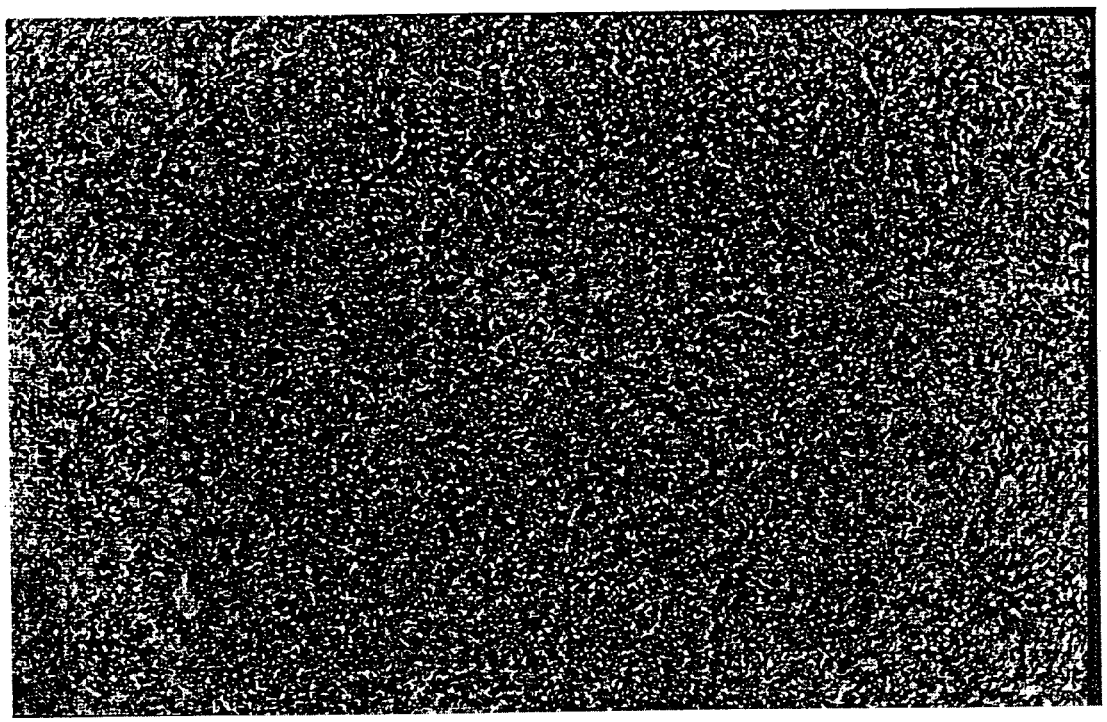
Figure 3D:
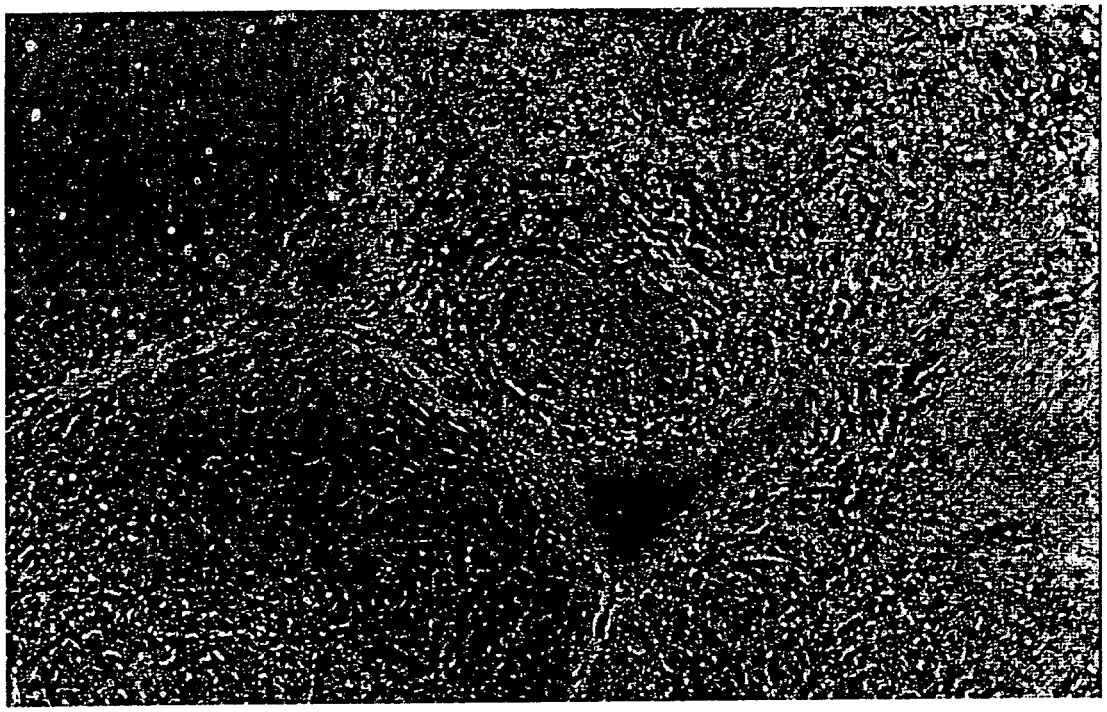

HES-1 or HES-2 cells described in PCT/AU99/00990 were subcultured in the presence or absence of insulin and maintained without subculture for periods of 1–4 weeks. Colonies of treated or control cells were harvested using dispase. Some colonies were used to determine the presence of transcripts for stem cell specific genes (October-4, Cripto, Genesis, GDF-3, GCNF) in the cultures by RT-PCR. Other colonies were dissociated to single cells and stained for the presence of stem cell specific markers such as the GCTM-2 antigen. The total number of cells per colony was determined and the percentage of stem cells present was assessed by flow cytometry. The effect of insulin on stem cell survival was assessed by assay of apoptosis on colonies. (See FIGS. 1 and 2).

Example 2

Action of Insulin on Long-Term Maintenance of Human Embryonic Stem Cells

HES 1 and HES-2 were cultivated for 10 passages in the presence of insulin. At this point, the cell phenotype was determined using immunochemistry and RT-PCR for stem cell markers, the karyotype was assessed by G-banding, and the ability to differentiate into various cell types was assessed by transplantation of cells into said mice and by immunostaining of cells grown to high density for various markers of specific differentiated cell types including neuronal and muscle cells.

Example 3

Effect of Insulin on Somatic Differentiation of Human ES Cells

HES1 and HES2 were subcultured in the presence of insulin and maintained for 3–6 weeks without further transfer. The extent of extraembryonic differentiation was assessed by morphological evaluation of the presence of squamous cells forming cystic vesicles. The extent of somatic differentiation was assessed by morphological assessment and by immunochemical staining for known markers of somatic cell lineages including neuronal markers. (See FIGS. 3 and 4).

Example 4

Basis of the Action of Insulin

To assess whether the actions of insulin were direct or mediated through the feeder cell layer, the following studies were carried out. The presence of receptors for insulin or IGFs on the stem cells was determined using RT-PCR or immunochemistry. The actions of insulin on stem cells grown in the absence of a feeder layer was determined using the methods described in 1 above. The effect of insulin treatment of the feeder layer was determined by treating a feeder cell layer with insulin, collecting the supernatant, removing the low molecular weight proteins including insulin using ultrafiltration, and testing the high molecular weight fractions for support of stem cell growth as described above (1); alternatively, an insulin treated feeder cell layer was extracted to yield an extracellular matrix preparation and stem cells were cultivated on this preparation and assessed for growth as described above (1). Identification of specific genes expressed in insulin treated feeder cell layers was carried out using standard molecular biology methods for comparison of gene expression in related cell types, such as representational display analysis.

Example 5

Isolation of Novel Subsets of Stem Cells with Desired Properties

Cells from control or insulin treated cultures were harvested, stained with antibodies GCTM-2 and TRA 1-60, and populations of cells bearing either marker only, both markers, or neither marker, were isolated by immunomagnetic beads or flow cytometry. These cells were cultured, and their colony forming ability and differentiation capacity was assessed. (See FIG. 1).

Example 6

Effect of noggin on Undifferentiated Embryonic Stem Cells

Undifferentiated stem cells were derived as in PCT/AU99/00990.

A recombinant form of the mouse BMP antagonist noggin, consisting of a signal peptide, the mouse noggin peptide from amino acid residues 20–232, a peptide linker, and the Fc region of human IgG1 (R&D Systems), was added in the dose range 100–500 ng/ml to cells grown under standard ES cell culture conditions.

Applicants have found that the default pathway of extraembryonic endoderm differentiation seen in ES cell cultures grown under standard conditions may be mediated by endogenous production of the growth and differentiation factor BMP (bone morphogenetic protein), a member of the transforming growth factor beta superfamily. Untreated cultures of ES cells grown under standard conditions express transcripts for both BMP and its receptors (FIG. 5).

Cultures treated with BMP will undergo differentiation into a cell type with a morphology similar to the flat squamous cells found in spontaneously differentiating cultures, and will express immunochemical markers and genes characteristic of this cell type (FIG. 6 and FIGS. 7A and B).

After approximately 5 days noggin treated cultures (100–500 ng/ml) consisted of colonies of distinct small round cells differing in appearance from ES cells (FIG. 8).

In contrast to control cultures, colonies in noggin treated dishes contained no flat squamous epithelial cells or cystic structures similar to those in BMP-2 treated cultures. The growth of the colonies was also inhibited in the presence of noggin, and the proportion of cells bearing the stem cell marker GCTM-2 was reduced compared to control cultures (FIG. 9). The noggin cultures were homogenous in appearance, though at later time points some showed a tendency to form palisade cell structures.

The immunophenotype of the noggin treated cells showed that they were distinguished by their lack of expression of a number of markers characteristic of ES cells or differentiated cells found spontaneously at early time points (7–10 days) following ES cell subculture under standard conditions. Thus the noggin induced cells are not reactive with the following antibodies: PHM4 recognising MHC Class 1 surface molecules, anti-desim, UJ13A reactive with polysialylated N-CAM, Cam 5.2 reactive with low molecular weight cytokeratins, AMF reactive with vimentin intermediate filaments, antibody to 160 kDa neurofilament protein, GCTM-2 reactive with a proteoglycan present on the surface of ES cells, TG42.1 reactive with a 25 kDa protein which copurifies with the proteoglycan recognised by GCTM-2 and is found on stem cells and other cell types, monoclonal antibody 5G7 reactive with an unknown molecule present on a small proportion of cells in spontaneously differentiating human EC cell cultures, and monoclonal antibodies BH6N and bTAN 20 reactive with human Notch 1 and Notch 2. However, a significant proportion of cells present in noggin treated cultures were reactive with an antibody recognising the 68 kDa neurofilament protein.

The noggin treated cells did not express genes characteristic of pluripotent ES cells, such as October-4 or cripto (FIG. 10). Neither did they express transcripts for markers of neuroectoderm, such as Pax-6 or nestin (FIG. 10). Thus, although the noggin cells could form neurospheres, they are probably not committed to that fate.

The noggin treated cells may be further characterised in biological assays. Addition of 25 ng/ml recombinant human BMP-2 along with 250 ng/ml noggin led to the appearance of squamous cells and cysts characteristic of spontaneously differentiating ES cell cultures or BMP-2 treated cultures, indicating that BMP-2 could antagonise the noggin effect. The noggin treated cells could be subcultivated under standard conditions for ES cell culture and retain their distinctive morphology under these conditions.

If the noggin treated cells were placed in neural progenitor culture medium, they formed structures with the appearance of neurospheres (FIG. 11) which could be maintained for at least two weeks in culture. This finding, along with the presence of cells expressing the 68 kDa neurofilament protein (FIG. 12) in noggin treated cultures, suggests that the noggin cells are capable of undergoing commitment to neurogenic lineages, in line with effects of noggin in early vertebrate embryos.

Thus, although the identity and differentiation potential of the cells induced by treatment of human ES cells with noggin has yet to be defined, the results show that an antagonist of BMP-2 can alter the outcome of differentiation of human ES cells, as predicted by the BMP autocrine loop model, and establish proof of principle that the control point regulating extraembryonic differentiation of ES cells is an important regulatory node in governing the fate of this cell. It may be that different antagonists, such as Gremlin or uncharacterised BMP antagonists, will also modify spontaneous differentiation of human ES cells, to enhance stem cell renewal or produce different forms of committed cell. The noggin results show for the first time a directed differentiation of human ES cells by a polypeptide into a homogenous cell population.

Finally it is to be understood that various other modifications and/or alterations may be made without departing from the spirit of the present invention as outlined herein.

What is claimed is:

1. A method of producing a human neural progenitor cell from a human ES cell, said method comprising:
   obtaining a source of an undifferentiated human ES cell; and
   culturing the ES cell in the presence of an antagonist of a BMP mediated default pathway of extra embryonic endoderm differentiation to differentiate the ES cell to a progenitor cell, wherein said progenitor cell lacks at least one marker of said undifferentiated ES cell; and
   culturing the progenitor cell in a neural progenitor cell culture medium to obtain a neural progenitor cell.

2. The method of claim 1 wherein the source of said undifferentiated human ES cell is selected from the group consisting of an embryo, a blastocyst, and a culture of undifferentiated embryonic stem cells.

3. The method of claim 2 wherein said antagonist is noggin.

4. The method of claim 3 wherein said noggin is a human or mouse noggin.

5. The method of claim 3 wherein said noggin is a mouse BMP antagonist noggin comprising amino acid residues 20 to 232 of mouse noggin.

6. The method of claim 3 wherein said noggin is in the range of 100 to 500 ng/ml.

7. The method of any one of claims 1 to 6 wherein the ES cell is differentiated to said progenitor cell is by culturing the ES cell in the presence of noggin for at least 5 days, wherein the noggin is in the range of 100 to 500 ng/ml.

8. The method of claim 1 wherein said at least one marker of said undifferentiated ES cell is October-4 or cripto.

9. A method of producing a human progenitor cell from a human ES cell, said method comprising:
   obtaining a source of an undifferentiated human ES cell; and
   culturing the ES cell in the presence of an antagonist of a BMP mediated default pathway of extra embryonic endoderm differentiation under conditions sufficient to differentiate the ES cell to a progenitor cell, wherein said progenitor cell lacks at least one marker of said undifferentiated ES cell, lacks a marker of neuroectoderm, and is capable of differentiating into a neural progenitor cell.

10. The method of claim 9 wherein said antagonist is noggin.

11. The method of claim 10, wherein the ES cell is cultured in the presence of noggin for at least 5 days.

12. The method of claim 10 wherein said noggin is a human or mouse noggin.

13. The method of claim 10 wherein said noggin is comprises amino acid residues 20 to 232 of mouse noggin.

14. The method of claim 10 wherein said noggin is in the range of 100 to 500 ng/ml.

15. The method of claim 9 wherein the source of said undifferentiated human ES cell is selected from the group consisting of an embryo, a blastocyst, and a culture of undifferentiated embryonic stem cells.

16. The method of claim 9, wherein said at least one marker of said undifferentiated ES cell is October-4 or cripto.

17. The method of claim 9, wherein said marker of neuroectoderm is nestin or Pax 6.

18. The method of claim 9, wherein said progenitor cell is unreactive with any one of the antibodies selected from the group consisting of PHM4 recognising MHC Class 1 surface molecules, anti-desmin, UJ13A reactive with polysialylated N-CAM, Cam 5.2 reactive with low molecular weight cytokeratins, AMF reactive with vimentin intermediate filaments, antibody to 160 kDa neurofilament protein, GCTM-2 reactive with a proteoglycan present on the surface of ES cells, TG42.1 reactive with a 25 kDa protein which copurifies with the proteoglycan recognised by GCTM-2 and is found on stem cells and other cell types, and monoclonal antibody GCTM-5 reactive with a molecule present on a small proportion of cells in spontaneously differentiating human ES cell cultures.

19. The method of claim 9, wherein said progenitor cell, upon further culturing in a neural progenitor culture medium, differentiates into said neural progenitor cell.

* * * * *